United States Patent [19]
Graves

[11] Patent Number: 5,156,426
[45] Date of Patent: Oct. 20, 1992

[54] NEEDLE GUARD

[76] Inventor: Alice M. Graves, 2826 N. Dorgenois, New Orleans, La. 70117

[21] Appl. No.: 686,928

[22] Filed: Apr. 18, 1991

[51] Int. Cl.$^5$ .............................................. A47F 13/06
[52] U.S. Cl. .......................................... 294/1.1; 294/2; 604/192; 604/263
[58] Field of Search ................ 604/192, 197–198, 604/263; 33/403, 404, 405, 411, DIG. 10; D19/35, 36, 37, 39, 40; 81/487; 294/1.1, 2, 10; 128/917, 919

[56] References Cited

U.S. PATENT DOCUMENTS

| | | | |
|---|---|---|---|
| D. 147,526 | 9/1947 | Brown | 33/27.01 |
| D. 279,797 | 7/1985 | Brunetto | D19/37 |
| 1,596,678 | 8/1926 | Miller . | |
| 2,077,232 | 12/1931 | Grahek | D19/39 |
| 2,298,635 | 10/1942 | Bliss | 33/41.2 |
| 2,507,073 | 5/1950 | White | D19/40 |
| 2,829,548 | 4/1959 | Byrd . | |
| 3,157,422 | 11/1964 | Sloan et al. | 294/106 |
| 4,345,381 | 8/1982 | Brislin | 33/DIG. 10 |
| 4,596,562 | 6/1986 | Vernon | 604/192 |
| 4,717,386 | 1/1988 | Simmons | 604/192 |
| 4,801,166 | 1/1989 | Jordan et al. | 294/10 |
| 4,834,716 | 5/1989 | Ogle, II | 604/192 |
| 4,852,844 | 8/1989 | Villaveces | 248/314 |
| 4,915,698 | 4/1990 | Levenson | 604/192 |

Primary Examiner—C. Fred Rosenbaum
Assistant Examiner—Ronald Stright, Jr.
Attorney, Agent, or Firm—David L. Ray

[57] ABSTRACT

In accordance with the present invention there is provided a hand held tool for connecting to an injection port of an intravenous administration set used to infuse a patient with an intravenous solution having apertures therethrough for receiving and removing the cover of a needle connected to a syringe and a handle for grasping by the user which is remote from the injection port, and a method for handling syringe needle covers during the injection of solutions into an injection port of an intravenous administration set.

9 Claims, 2 Drawing Sheets

NEEDLE GUARD

BACKGROUND OF THE INVENTION

1. Field of the Invention

The present invention is related to medical appliances. More particularly, the present invention is related to devices used with hypodermic syringes for preventing an undesired penetration of the flesh by a hypodermic syringe needle.

2. Description of the Prior Art

Mechanisms and devices for holding insertable items including needles used with hypodermic syringes are well known in the art. Exemplary of such prior art are the following U.S. Patents:

U.S. Pat. No. 4,915,698 discloses a device for removing and replacing a protective cover on a needle of a hypodermic syringe. The device includes a base member having a generally planar bottom surface together with a device for securing the bottom surface to an external flat surface. A tubular member extends from the base member at a predetermined angle relative to the planar bottom surface. The tubular member includes an open end for receiving axially a needle with a protective cover and an inner surface defining an elongated cylindrical cavity having an inner diameter slightly larger than the maximum diameter of the protective cover to be received therein. Tabs extending inwardly from the inner surface of the tubular member are provided to operably engage a lip on the protective cover when the cover is within the cavity. The lip is operable to engage at the tab when the protective cover is urged thereagainst whereby the protective cover remains within the tubular member while needle is removed therefrom. Reinsertion of the needle into the device replaces the protective cover thereon wherein the used needle may be safely disposed of or reused.

U.S. Pat. No. 4,852,844 disclosed a device for aiding a nurse in the preparation and set up of intravenous therapy. The device has a backing plate with a backing layer of adhesive for securement to an IV pole, the backing plate being made of a flexible material so that it may be wrapped about the IV pole. A frustro-conical hollow member is supported by the front surface of the backing plate in which are provided friction-gripping ribs to firmly hold and grip a needle-cap of an intravenous needle, so that when the needle and its cap are inserted into the hollow the cap is firmly held, after which the needle proper may be removed from the cap for subsequent IV therapy. The device allows a nurse to accomplish such needle and cap separation with only one hand, to free her other hand to hold another part of the IV set-up or to perform another task.

U.S. Pat. No. 4,834,716 discloses a protective device for enclosing the scarf of a cannula carried by a boss while permitting access to the said scarf by a port of a Y-site which is located into proximity to an adjoining length of flexible tubing forming part of an intravenous administration set. The protective device has a cylindrical sheath portion surrounding the cannula, the ends of the cylindrical portion having at least one cutout which snugly receives the flexible tubing.

U.S. Pat. No. 4,717,386 discloses a safety device for a needle which includes a sheath reception opening provided in a cap retainer member of provided in a hand shield portion of the device. The cap retainer member in one embodiment is joined to the hand shield section and in another embodiment is secured to a pair of legs joined at right angles. In another embodiment the cap retainer member is used by itself with an adhesive provided on a base surface thereof. A manually engageable gripping portion is provided at the base surface of the hand shield portion in another embodiment, with a handle extending from the gripping portion beyond the periphery of the hand shield portion. In a further embodiment the handle extends from the hand shield portion, In another embodiment a plurality of cap retainer members are joined to the hand shield portion. In still another embodiment a sheath holding opening is provided in the handle portion. Some embodiments of the safety device can be hand-held and used on a support surface. Other embodiments can be used only on a support surface. All embodiments permit the hand which normally holds the protective sheath of a syringe to be isolated from a zone of high risk. Embodiments of the device that are secured to a support surface can be operated with one hand. Use of the handle to stabilize the device on a support surface further isolates the hand from the zone of high risk.

U.S. Pat. No. 4,596,562 discloses a safety device and method for handling syringe needle covers. There is disclosed a hand tool for holding a syringe needle cover which prevents accidental pricking when it is replaced, and comprises a slot between parallel plates, into which the needle cover flange can be wedged. Tapered needle covers are gripped by holes in the tool, providing a safe method for handling syringes.

U.S. Pat. No. 3,157,422 disclosed a hand implement usable to pick objects from the ground and more specifically to a hand implement having a pair of spring biased fingers which are operable to grip and retain elongated objects such as sticks or twigs lying upon the ground.

U.S. pat. No. 2,829,548 disclosed a wrench for holding and inserting bushings. This invention relates to a bushing-inserting tool and more particularly to a wrench for inserting washers or bushings in relatively inaccessible places. The tool includes a handle, a pair of spaced plates at one end of the handle for receiving a bushing between them, and a resilient device positioned between the plates for holding such bushing between the plates, the tool having a passage communicating with the space between the plates through which a bushing may be passed to position it in engagement with the resilient device and another passage communicating with the first passage whereby a post may be entered into a bushing to strip such bushing from the tool.

U.S. Pat. No. 1,596,678 discloses a washer-handling tool designed to take care of such valve spring tension maintaining devices as fall within the class employing secondary washers. The most common of the forms of washers thus employed is the U-shaped washer. The tool includes a handled shank having a head at its operative end, the head including a pair of spring fingers adapted to grasp a washer edgewise and to permit the washer being pushed from between the fingers in a direction at right angles to the plane occupied by the washer and fingers, with washer receiving palette located between and independent of the fingers and adapted to support a washer thereon.

SUMMARY OF THE INVENTION

In accordance with the present invention there is provided a hand held tool for selectively connecting to an injection port of an intravenous administration set used to infuse a patient with an intravenous solution, the hand held tool having apertures therethrough for receiving and removing the cover of a needle connected to a syringe and a handle for grasping by the user which is remote from the injection port. Additionally, there is provided a method for handling syringe needle covers and positioning the injection port during the injection of solutions into an injection port of an intravenous administration set.

The hand held tool of the invention aids in the prevention of accidental needle sticks which might cause infection of the user by contaminants on the needle.

Furthermore, the hand held tool of the invention removes and holds the syringe needle cover, allowing quicker and more efficient injection through the injection port.

An additional advantage of the hand tool of the invention is that it has no moving parts, and is therefore low in cost.

BRIEF DESCRIPTION OF THE DRAWINGS

FIG. 3 is a perspective view of the tool of the invention held by the user, and

DESCRIPTION OF THE PREFERRED EMBODIMENTS

Figure 1:
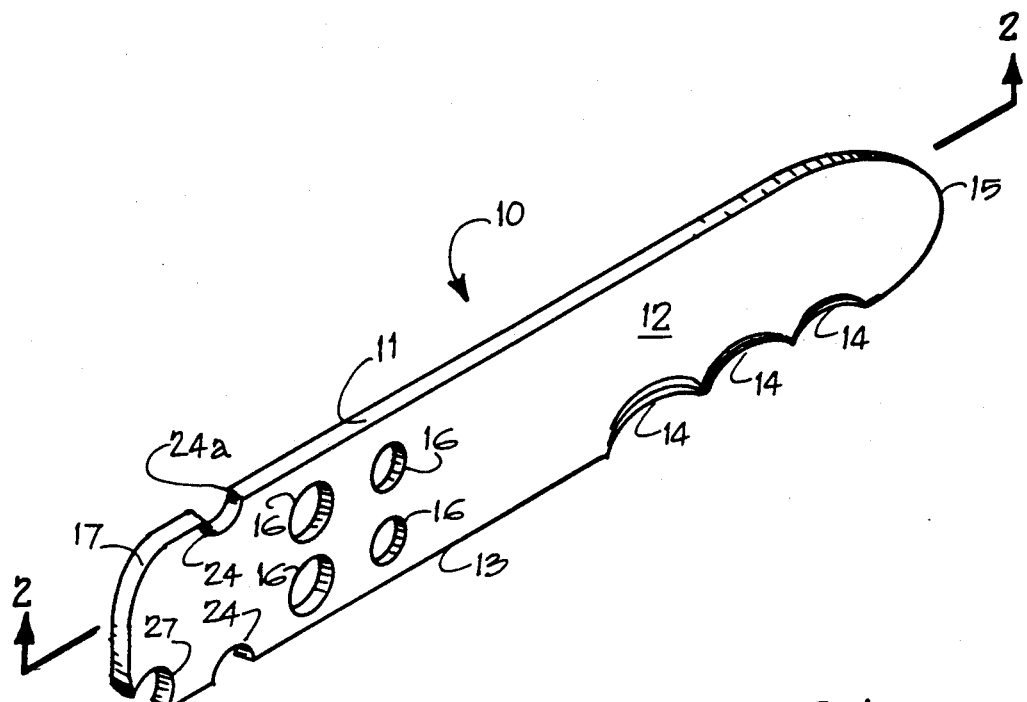
FIG. 1 is a perspective view of tool of the present invention.

Referring now to the drawings, in FIG. 1 is shown the hand tool of the invention generally indicated by the numeral 10. Tool 10 is preferably molded or made from a single flat rectangular continuous plate of rigid material such as plastic, although tool 10 could be machined or stamped from a metal such as steel, or tool 10 could be cut from a single piece of wood. Tool 10 is generally rectangular in shape and has an upper straight edge 11 which is generally parallel to bottom straight edge 13, with the two ends 15 and 17 having generally rounded corners. The tool preferably is about seven to ten inches in length and about one inch in width, with a thickness of about one-eighth to about one-sixteenth of an inch.

Figure 2:
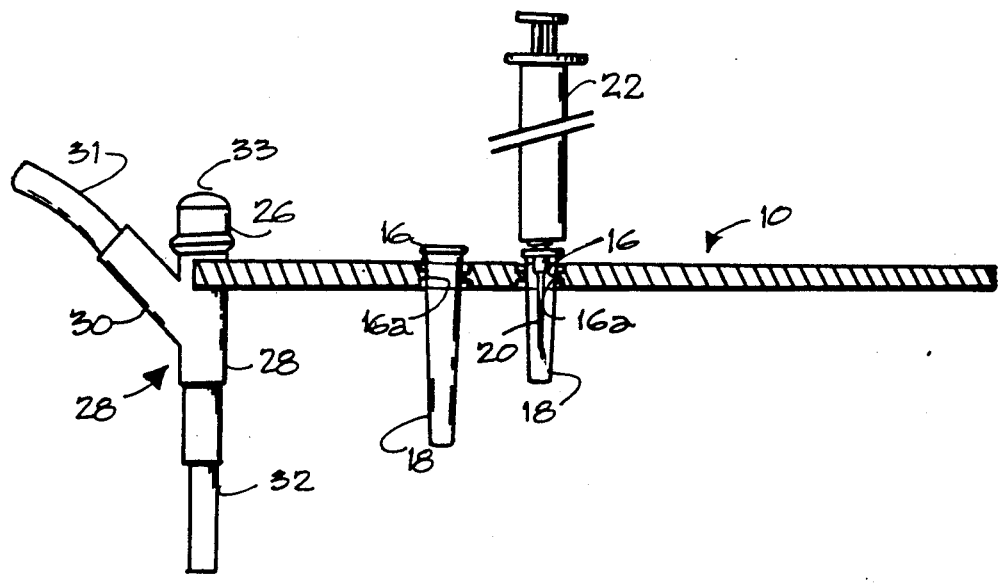
FIG. 2 is a cross-sectional view taken along lines 2—2 of FIG. 1.
Figure 5:
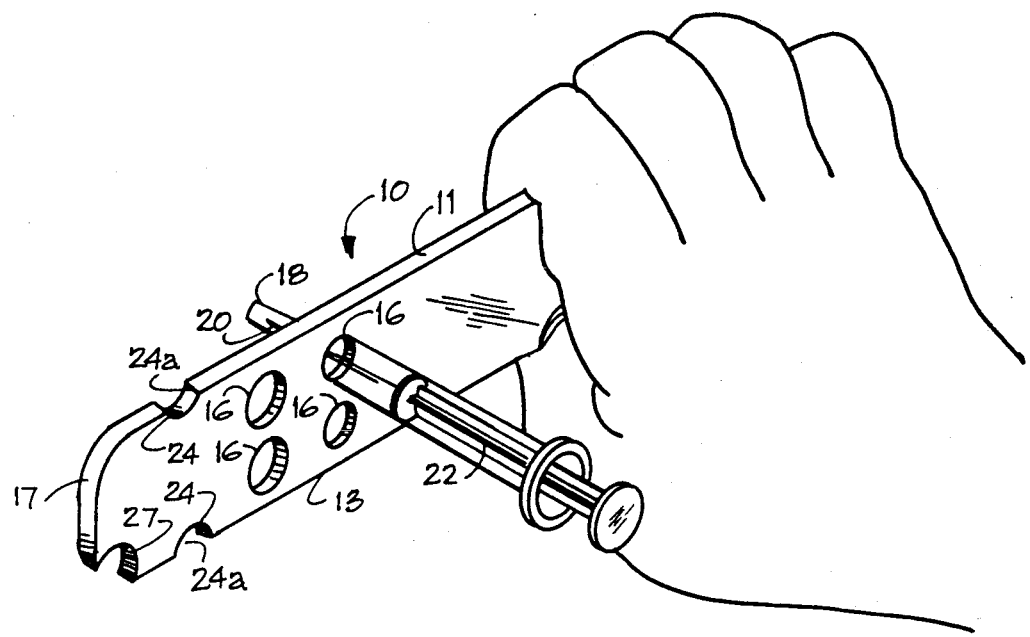

Tool 10 has a handle portion 12 which may have recesses 14 for receipt of the fingers of the user, although the recesses 14 could be deleted if desired. Adjacent to handle portion 12 are a plurality of apertures 16 for receipt of a plurality of conventional needle covers 18 which are used to cover hypodermic needle 20 connected to syringe 22 as shown in FIG. 2. Needle 20, syringe 22, and needle cover 18 are commonly used in health care and are well known in the art. The needle covers 18 shown in the drawings are made from clear, transparent plastic.

Apertures 16 are sized sufficiently small to permit a standard needle cover 18 to be force fitted therein. Circular protuberances 16a shown in FIG. 2 may be located inside apertures 16 to increase the frictional forces on needle covers 18, although the protuberances may be eliminated, if desired.

Figure 4:
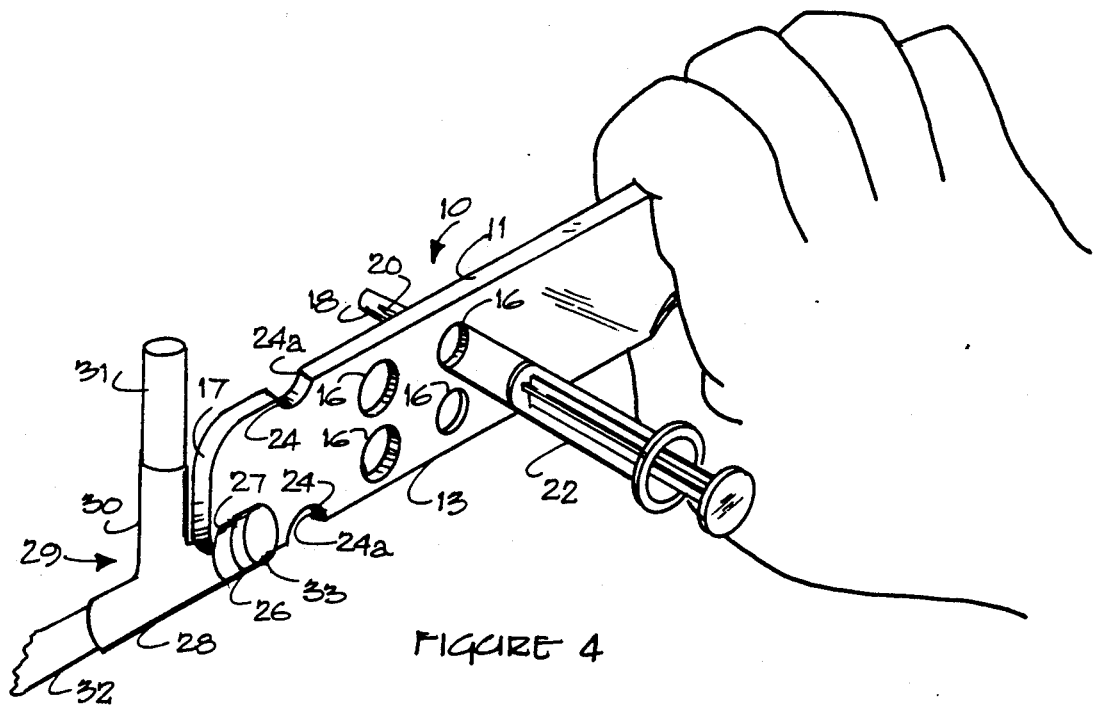
FIG. 4 is a perspective view of the tool of the invention connected to an injection port.

Located on opposite outer edges of the end of tool 10 adjacent to apertures 16 are semi-circular slots 24—24 having openings 24a therein. A single semi-circular slot 24 may be provided if desired, although two slots may make the tool easier to use. Slots 24 are sized to receive and hold hollow tube 26 or injection port 30a of a standard intravenous administration set or Y-site generally indicated by the numeral 29. If desired, the two slots may have different diameters. Preferably semi-circular slots 24—24 and 27 have a circumferential length slightly longer than a semi-circle and a diameter slightly less than the diameter of the components of Y-site 29 to hold Y-site 29 therein after Y-site is force-fitted into slot 27 as shown in FIG. 4, or into slots 24—24.

Located on the outer edge of the end of tool 10 opposite the handle portion 12 is semi-circular slot 27. Slot 27 facilitates the use of tool 10 when it is necessary to inject solutions with a syringe into injection port 33 of conventional intravenous administration or Y-site 29 which is connected by tube 32 to a needle (not shown) implanted directly in the patient's arm or other body part. Such needles are sometimes left in a patient's arm for a period of time to convey liquids received through tube 31 and inlet 30, and during this period of time it may be desired to inject the patient with a needle and syringe through the needle left in the patient's body. Accordingly, the semi-circular slot 27 may be force fitted around the device left in the patient's body prior to injection while the user holds the handle.

The nurse, doctor, or other medical personnel can use the hand held tool 10 of the invention to grasp the injection site rather than grasping the injection site by the fingers of one hand while holding the syringe in the other hand. Thus the fingers of the user need not grasp the injection port 30 while inserting needle 20 into the injection port 30. Furthermore, slot 27 provides the same advantages when the tube 26 has been disconnected and an injection port or needle is left in the body of the patient.

Furthermore, medical personnel can use tool 10 to hold the needle 20, needle cover 18, and syringe 22 as shown in FIGS. 1, 2, and 3. After inserting the needle cover 18 into one of the apertures 16—16, the aperture 16 or protuberances 16a grasp the needle cover 18 and hold the needle cover while the syringe and exposed needle is withdrawn from tool 10 and needle cover 18. The needle 20 is then exposed to make the desired injection, and the injection site 30a is firmly held in semi-circular slot 27. Thus the hand of the user shown in FIGS. 3 and 4 is sufficiently far away from the injection site 30a to aid in preventing the hand or fingers of the user from being stuck by the needle 20. Furthermore, the same tool 10 can be used four times to store needle covers in all four apertures 16.

Although the preferred embodiments of the present invention have been disclosed and described in detail above, it should be understood that the invention is in no sense limited thereby, and its scope is to be determined by that of the following claims:

What is claimed is:

1. A hand held tool for connection to an injection port of an intravenous administration set used to infuse a patient with an intravenous solution to guard the user from sticking herself with a needle comprising:
   a. a generally rectangular rigid flat plate, said plate having a first end and a second end, said first end of said plate being adapted to be grasped by one hand of the user, said two long edges comprising a top edge and a bottom edge generally parallel to each other,
   b. holding means located said second and of in said plate for receiving and holding an injection tube into which a hypodermic needle connected to a syringe is be inserted, said holding means comprising semi-circular slots on the edge of the plate into which said injection tube may be selectively inserted and held, said semi-circular slots extending completely through said second end of said plate to enable said injection tube to extend completely through said second end of said plate, and c. a plurality of aperture means in said plate for receiving, grasping, and holding tubular needle cover means.

2. A hand held tool for connection to an injection port of an intravenous administration set used to infuse a patient with an intravenous solution to guard the user from sticking herself with a needle comprising:

a. a generally rectangular rigid flat plate, having two long edges and two short edges said plate having a first end and a second end, located at opposite ends of said long edges said first end of being adapted to be grasped by one hand of the user, b. holding means located in said second end of said plate for receiving and holding an injection tube into which a hypodermic needle connected to a syringe is be inserted, said holding means comprising semi-circular slots on the edge of said second end into which said injection tube may be selectively inserted and held, said semi-circular slots extending completely through said second end of said plate to enable said injection tube to extend completely through said second end of said plate, and c. a plurality of aperture means in said plate for receiving, grasping, and holding tubular needle cover means.

3. The hand held tool of claim 2 wherein said slots are sized to require said injection tube to be force fitted therein.

4. The hand held tool of claim 2 wherein said apertures have friction means therein for grasping said needle cover means.

5. The hand held tool of claim 4 wherein said friction means are protuberances connected to the inside wall of said apertures.

6. The hand held tool of claim 2 wherein said generally rectangular plate has two long edges and two short edges, wherein said two long edges comprise a top edge and a bottom edge generally parallel to each other.

7. The hand held tool of claim 6 wherein said holding means is located in said bottom edge of said plate.

8. The hand held tool of claim 7 wherein said holding means is located in said top edge and said bottom edge of said plate.

9. The hand held tool of claim 7 wherein said holding means is located in said top edge of said plate.

* * * * *